United States Patent [19]
Carangelo et al.

[11] Patent Number: 4,824,790
[45] Date of Patent: Apr. 25, 1989

[54] SYSTEM AND METHOD FOR THERMOGRAVIMETRIC ANALYSIS

[75] Inventors: Robert M. Carangelo, Coventry; Peter R. Solomon, West Hartford, both of Conn.

[73] Assignee: Advanced Fuel Research, Inc., East Hartford, Conn.

[21] Appl. No.: 920,846

[22] Filed: Oct. 17, 1986

[51] Int. Cl.[4] .................. G01N 21/35; G01N 21/75; G01N 25/00

[52] U.S. Cl. ........................... 436/157; 422/80; 422/94; 422/98; 436/155; 436/160

[58] Field of Search ............ 422/78, 80, 81, 94, 422/98; 436/155, 160, 157; 250/343

[56] References Cited

U.S. PATENT DOCUMENTS

| | | | |
|---|---|---|---|
| 3,167,396 | 1/1965 | Staunton et al. | 422/78 |
| 3,173,762 | 3/1965 | Varadi et al. | |
| 3,186,801 | 6/1965 | Hampton | |
| 3,281,597 | 10/1966 | Greenberg | 250/343 |
| 3,861,874 | 1/1975 | Krc | 422/80 |
| 3,985,505 | 10/1976 | Bredeweg | 422/78 |
| 4,094,797 | 6/1978 | Newkirk et al. | 8/115.6 |
| 4,106,908 | 8/1978 | Leplat-Gryspeerdt | |
| 4,150,951 | 4/1979 | Capelle et al. | 422/78 |
| 4,229,412 | 10/1980 | Orths et al. | 422/78 |
| 4,244,917 | 6/1981 | Woods et al. | 422/78 |
| 4,331,445 | 5/1982 | Burns | 44/1 R |
| 4,352,673 | 10/1982 | Espitalie et al. | |
| 4,519,983 | 5/1985 | Espitalie et al. | 422/78 |
| 4,554,132 | 11/1985 | Collins | 422/78 |
| 4,652,755 | 3/1987 | Solomon et al. | 250/341 |

FOREIGN PATENT DOCUMENTS 1912526 10/1970 Fed. Rep. of Germany ........ 422/80

OTHER PUBLICATIONS

Solomon et al., Amer. Chem. Soc., vol. 31, No. 1, Preprints of Papers, Apr. 13–18, 1986, pp. 1–5.

Primary Examiner—Barry S. Richman
Assistant Examiner—Timothy M. McMahon
Attorney, Agent, or Firm—Ira S. Dorman

[57] ABSTRACT

An instrument for the chemical analysis of coal and other hydrocarbons combines TGA and FT-IR principles, and utilizes helium to carry the volatiles evolved by pyrolysis of the sample into the optical cell of the FT-IR spectrometer. The connection between the TGA furnace and the optical cell is substantially direct and non-impeding to fluid flow, and the carrier gas is preheated to the same temperature as the sample, preferably using a common heating element.

25 Claims, 2 Drawing Sheets

SYSTEM AND METHOD FOR THERMOGRAVIMETRIC ANALYSIS

BACKGROUND OF THE INVENTION

A number of thermal analysis methods have heretofore proven useful for probing the organic and mineral composition of insoluble hydrocarbon materials, such as coal, char, tar, lignins, wood, polymers, oil shale and petroleum source rock. Such techniques typically include subjecting the sample to dynamic pyrolysis conditions (normally, increasing the temperature at a constant rate), while monitoring weight loss and product evolution. For example, thermogravimetric analysis (TGA) has been carried out for the proximate analysis of coal, pyrolysis with detection of total hydrocarbons has been used for petroleum source rock evaluation, and pyrolysis with recovery of evolved products has been utilized for analysis of source rocks and sediments by gas chromatography. Non-optical thermal equipment, known as the Rockeval instrument used for total hydrocarbon analysis, is also commercially available.

A need exists, however, for a high-speed analytical instrument which more effectively provides information regarding composition, structure, and reaction mechanisms and kinetics for hydrocarbon materials, and particularly with respect to heavy, tarry constituents.

It is of course well known to utilize electromagnetic radiation for a variety of analytical purposes. A particularly effective tool of this nature is the Fourier-transform infrared (FT-IR) spectrometer, which utilizes wavenumber-dependent absorption data to permit the analysis of various properties of many different substances. Particularly unique and valuable applications for such apparatus are described and claimed in copending U.S. patent application Ser. No. 690,301, entitled "Method and Apparatus for Analyzing Particle-Containing Gaseous Suspensions" and filed on Jan. 10, 1985 in the names of Solomon, Carangelo and Best, which is of common assignment herewith. That application has now issued as U.S. Letters Patent No. 4,652,755, and the same subject matter was published on Jul. 17, 1986 as International Publication No. WO86/04140 under the Patent Cooperation Treaty. The description of the FT-IR spectrometer set forth therein, with reference to FIG. 1, is hereby incorporated into this disclosure by reference thereto.

Analytical apparatus have previously been proposed which couple the principles of TGA and FT-IR techniques. However, such instruments have not proven entirely satisfactory from a number of standpoints; this is particularly so in regard to the physical relationship between the TGA furnace and the FT-IR cell, and the structure through which the volatilized fractions of the sample must pass. Thus, in such earlier apparatus, difficulties have been encountered in ensuring that all products evolved are reliably introduced into the cell, and that the physical state or form thereof is optimal for the spectrometric analysis. Moreover, the information that is obtainable by use of such a technique and instrument has not heretofore been fully appreciated or utilized to maximum advantage.

Accordingly, it is an object of the present invention to provide a novel apparatus and method by which solid and liquid materials can be analyzed at a high rate of speed, to provide information concerning composition, structure, reaction mechanisms and kinetics, and the like.

It is a more specific object of the invention to provide such a method and apparatus wherein principles of thermogravimetric and Fourier-transform infrared analyses are combined in a highly effective and desirable manner, which apparatus may be self-calibrating.

It is also an object of the invention to provide such an apparatus in which products evolved by pyrolysis of the sample are introduced into an optical cell completely and in an optimal form for analysis.

A further more specific object of the invention is to provide such an apparatus and method, which are particularly well-suited for the analyses of typical insoluble hydrocarbons.

Additional objects of the invention are to provide a novel apparatus an method for performing proximate and ultimate analyses of coal, for performing analogous analyses of other substances, and for enabling determinations of calorific value, char reactivity, active site density, sulphur form identification, and other characterizing features of such materials.

SUMMARY OF THE INVENTION

It has now been found that certain of the foregoing and related objects of the invention are readily attained by the provision of analytical apparatus comprised of a furnace, an optical analysis cell, heating means and weighing means. The furnace has an internal chamber and the analysis cell has an enclosed cavity, both with an inlet and an outlet for fluid flow, and the cell cavity is in substantially direct flow communication with the furnace chamber through the inlet and outlet thereof, respectively. The heating means includes a heater having elements which define a portion of the flow path through the furnace chamber, as well as temperature control means. A balance and a sample holder are provided by the weighing means, the latter being suspended from the balance and positioned within the furnace chamber at a location along the path portion that is defined by the heater elements. The holder is also spaced from the chamber inlet a distance sufficient to preheat gas flowing along that path to substantially the temperature of the heater elements prior to contact with the sample. An important feature of the apparatus is that it is substantially free of constricting or turbulence-creating structure along the path through the furnace, from the vicinity of the sample holder location, and through the chamber outlet and the cell cavity inlet (turbulence below the sample holder may be desirable for optimal heat transfer to the carrier gas).

In the preferred embodiments, the furnace chamber will be of elongated and generally rectilinear form, and vertically oriented with the inlet disposed adjacent its lower end and the outlet at its upper end. The optical analysis cell will normally have means for heating is to a temperature above 100° Centigrade to prevent water condensation, and will advantageously be adapted to pass electromagnetic radiation through the cavity along axes that are substantially perpendicular to the longitudinal axis of the furnace chamber. Most desirably, the cell will be connected directly to the top of the furnace, and the chamber outlet and the cavity inlet will be of substantially the same cross-sectional area. The optical cell will generally be elongated, in a direction substantially perpendicular to the axis of the furnace cavity, and it will have its inlet and outlet adjacent its opposite ends and disposed at the top and bottom, respectively, of the cavity.

The apparatus will usually include temperature sensing means disposed adjacent the bottom of the sample holder, and the weighing means will normally be adapted to generate an electrical signal that is indicative of the weight change of the sample contained within the holder, as a function of time. In certain embodiments, the furnace will have a second inlet to its chamber, disposed along the path therethrough beyond the location of the sample holder in the downstream direction of normal fluid flow. The heating means employed in such apparatus will desirably include a second heater having elements disposed between the first-mentioned heater elements and the outlet from the furnace chamber, and defining a second path portion adjacent the first and coaxially aligned with it; the second gas inlet will be disposed substantially at the intersection of the two path portions. The second heater elements will be adapted to heat fluid flowing along the second path portion, and the temperature control means will be adapted to independently control the temperatures of the first and second heaters. Most desirably, the apparatus will include a Fourier-transform infrared spectrometer system operatively connected to the optical cell.

Other objects of the invention are achieved by the provision of a method in which a sample of the material to be analyzed is supported within the chamber of a furnace and is heated to pyrolysis temperature. A carrier gas will be preheated to substantially the temperature desired for the sample, and will be swept therethrough so as to produce a mixture with the volatiles evolved by pyrolysis of the sample, and to provide a portion of the thermal energy required; preferably, the carrier gas will have a high coefficient of thermal conductivity and a low heat capacity, and most desirably it will be helium. The mixture is introduced substantially directly from the furnace chamber into the cavity of the optical analysis cell, wherein the varying composition of the volatiles is determined as a function of time. The weight change of the sample is also monitored as a function of time, and those data are correlated to the dynamic compositional data for analysis of the sample. In certain instances, this will be done for self-calibration purposes.

In the preferred embodiments of the method, the temperature will be increased at a constant rate, and generally the same thermal energy radiator, provided within the furnace chamber, will be utilized for heating both the gas and the material sample. The analysis cell will normally be heated to a temperature of 100° to 150° Centigrade, and the method will most beneficially be carried out so as to quickly bring the gaseous mixture to that temperature upon exit from the furnace chamber. As a result, any fractions of the volatiles evolved which condense at higher temperatures will form particles that are less than five microns, and preferably on the order of one to two microns in size, and the mixture will enter the analytical cell cavity in the form of an aerosol.

The method may also be carried out with the additional step of introducing a quantity of oxygen into the mixture of carrier gas and volatiles prior to their entry into the analysis cell cavity. As a further modification, oxygen may be introduced into the residue in the sample holder that remains following substantially complete pyrolysis of the sample, for ultimate analysis of the char or other residue.

DETAILED DESCRIPTION OF THE ILLUSTRATED EMBODIMENTS

Figure 1:
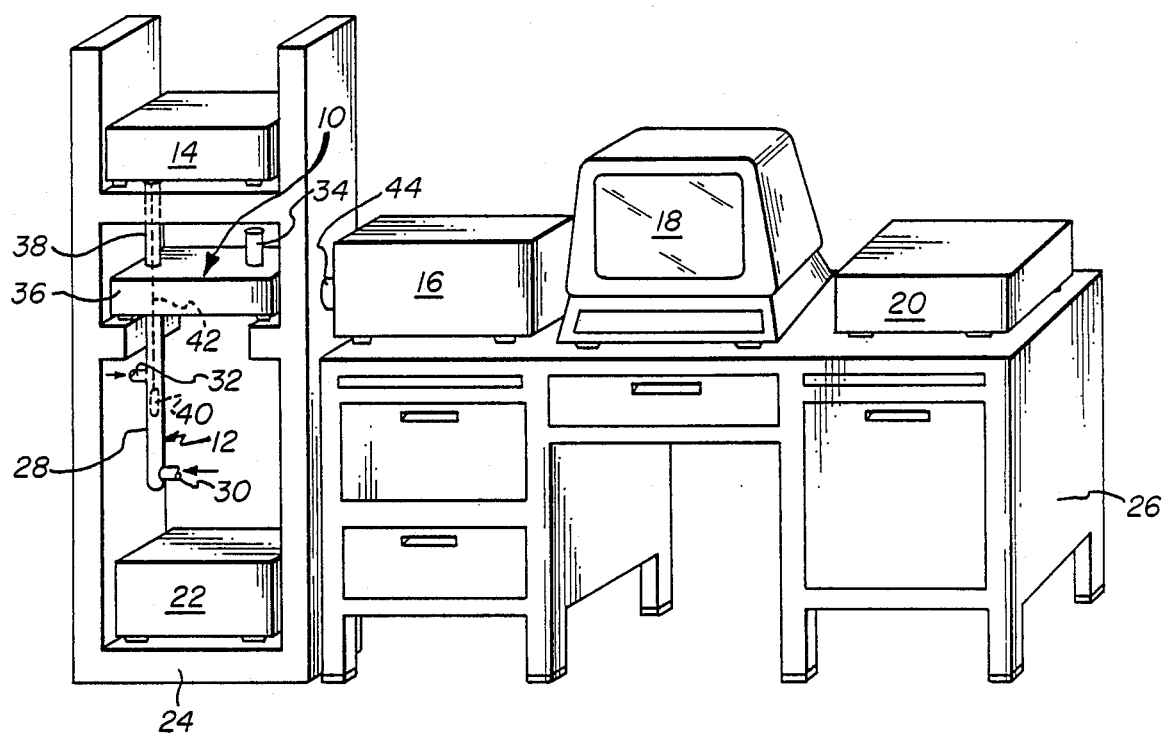
FIG. 1 is a schematic representation of a system embodying the present invention.

Turning now in detail to FIG. 1 of the appended drawings, the illustrated system embodies the invention and constitutes an analytical work station, including an optical cell unit, a furnace, a balance, an FT-IR bench unit, a computer, a combined printer and plotter unit, and a power supply, generally designated respectively by the numerals 10, 12, 14, 16, 18, 20 and 22. The optical cell unit 10, the balance 14 and the power supply 22 are supported within a vertical shelf-like stand 24, and the bench unit 16, computer 18 and printer/plotter 24 are conveniently placed upon a desk 26.

The furnace 12 comprises a cylindrical quartz tube 28 from the optical cell unit 10, and it has two pipes 30, 32 leading into it. An exhaust conduit 34 is provided at the end of the cell unit 10 opposite to that at which the furnace tube 28 is attached, and is upwardly directed and connected to an external exhaust vent. A second conduit 38 is disposed in coaxial alignment over the tube 28 and also extends upwardly providing communication between the cell unit 10 and the balance 14. A sample holder 40 is suspended by a wire 42 from the bottom of the balance 14 within the tube 28, the wire 42 passing through the conduit 38 and the optical cell 10; the latter includes a protective enclosure 36.

The FT-IR bench unit 16 is connected through a short barrel 44 to the cell unit 10, which affords an optical path therebetween. Although not illustrated, it will of course be appreciated that suitable electrical connections are provided among the several component so as to enable the analytical work station to function in the manner herein described.

Figure 2:
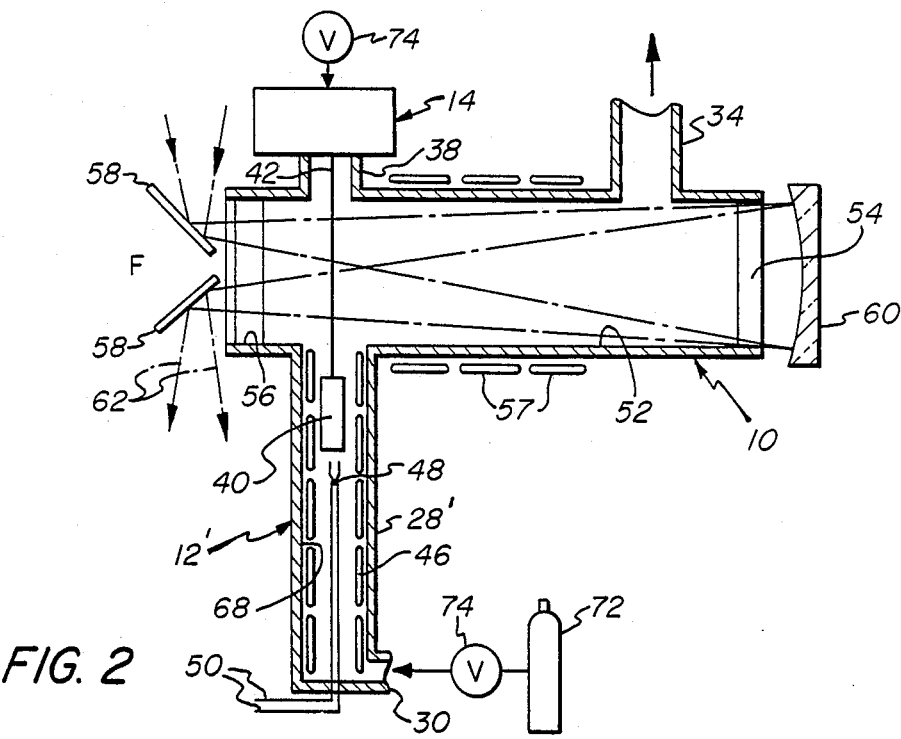
FIG. 2 is a schematic representation, in partial section, of the furnace, optical analysis, and balance components of a system of the type shown in FIG. 1, but wherein the furnace has only one inlet pipe.
Figure 3:
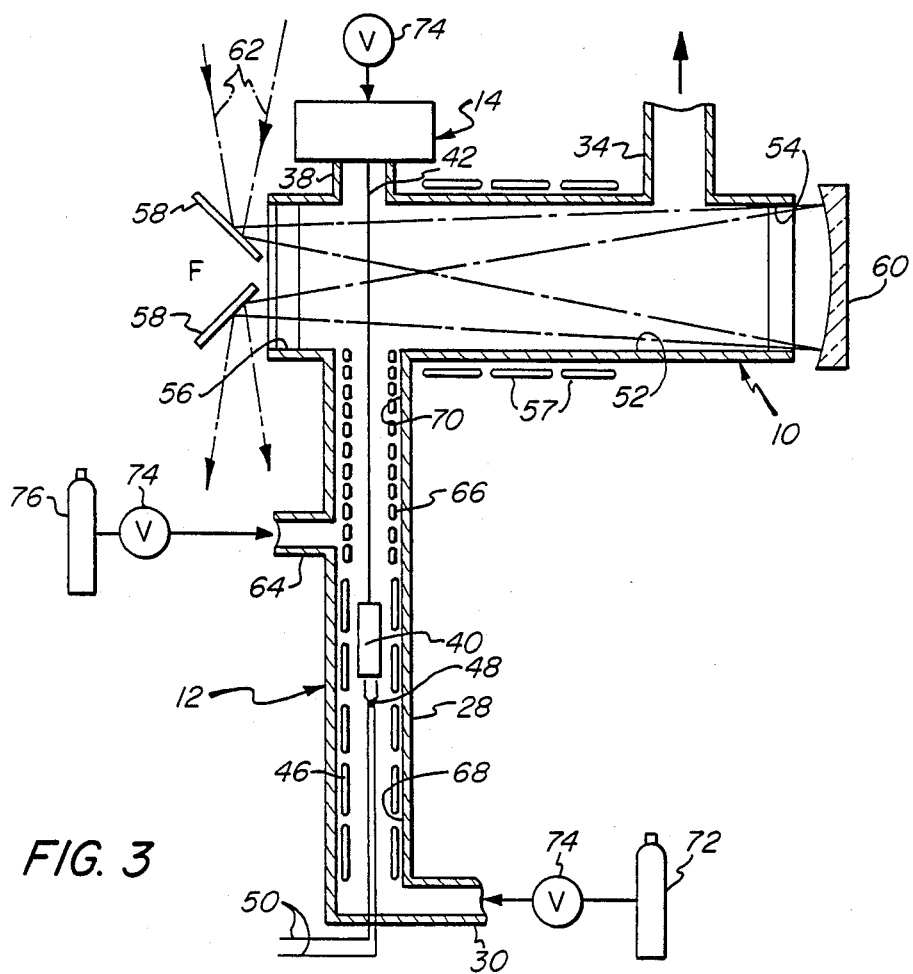
FIG. 3 is a view similar to FIG. 2, showing the same components but wherein the furnace is augmented, as in FIG. 1, to extend the utility of the system.

Turning now in greater detail to FIGS. 2 and 3, the heating, weighing and optical components of the system of Figure 1 are more fully illustrated. As can be seen, the furnace 12 or 12' includes a heating element 46 in the form of a generally cylindrical coil or cylinder, which is aligned coaxially within the bore of the tube 28 or 28'. The sample holder 40 is disposed with the upper end portion of the heating element 46, and an inlet pipe 30 communicates with the lower end thereof. A thermocouple 48 is also disposed within the heating element 46 and is positioned to lie closely adjacent the bottom of the sample holder 40; lines 50, for electrical connection of the thermocouple 48, are indicated.

The cell of the optical unit 10 provides a cylindrical chamber 52 having optical ports 54, 56 at its opposite ends; a heating coil is indicated at 57. Outwardly out of the port 56 are a pair of angled mirror elements 58, and a concave mirror element 60 is disposed outwardly of the port 54. The optical system is such that the beam of radiation 62 impinges upon the mirrored surfaces of the elements 58 and is reflected from the mirror 60, providing a focus position "F" between the elements 58.

The arrangement of FIG. 3 is similar to that of FIG. 2, the difference residing in the provision of the second gas introduction pipe 32 and second heating coil 66. As will be noted, the pipe 32 and coil 66 are both disposed above the level of the sample holder 40; the pipe 32 opens slightly above the intersection of the coils 46, 66, so that the gas discharged from it passes through the upper of the two. It will be appreciated that the heating elements 46, 66 are connected (by means not shown) to the power supply 22 in such a manner as to enable different temperatures to be established in the lower and upper zones 68, 70, respectively, of the tube 28, and independently varied.

The apparatus of the invention is utilized by initially placing the material to be analyzed into the sample holder 40, which will conveniently be a stainless steel, quartz or alumina mesh basket for a particularte sample, as will generally be its preferred form. After suspending the holder 40 within the upper portion of the passageway through the heating element 46, in the position shown in the Figures, the power to the heater will be turned on.

Operation of the appropriate valve 74 will then permit the carrier gas to flow (typically at a rate of 0.5 to 2 liters per minute) from the tank 72 through the inlet pipe 30 and upwardly along the path portion 68 defined within the quartz tube 28, 28', causing the gas to be heated by the portion of the element 46 downstream of the sample location. Because of this preheating of the gas through the initial length of the heater, the use of the same element to heat the sample in the holder 40, and the shielding that the heater provides for the sample, a highly stable temperature condition is provided, thus maximizing the accuracy and reliability of the analysis carried out. The thermocouple 48 serves of course to sense the actual temperature, proximate the sample holder, and to provide an electrical signal that is indicative thereof. Typically, the temperature will be increased during the run from ambient to 900° Centigrade, at the rate of 30 Centigrade degrees per minute; higher ultimate temperatures will generally be desirable (on the order of 1200° or so), consistent with the provision of a heating element capable of producing them as a practical matter.

As the sample heats, it eventually reaches a temperature at which pyrolysis will commence, the volatiles evolved becoming mixed with the carrier gas moving upwardly through the furnace. This fluid mixture is of course introduced directly into cavity 52 of the analysis cell, wherein its composition is determined on a dynamic basis; the fluid exits from the cell cavity through the conduit 34. The FT-IR bench unit 16 of course includes the optical system for generating an electromagnetic beam of wavenumbers varying in the infrared spectrum, and for intercepting it, after projection through the cell cavity 52, at a focal point in the region F, indicated in FIGS. 2 and 3. Absorption curves, qualitatively and quantitatively representative of composition, can then be plotted directly, by use of the FT-IR computer 18 and the printer/plotter 20.

As pyrolysis of the sample proceeds, the weight loss is dynamically determined by the balance unit 14, which provides a signal to the FT-IR computer 18 representative thereof. These data may similarly be printed and/or plotted in appropriate form by the unit 20; they may also be used internally for calibration of the system, by determining and introducing any correction factor that may be necessary into the extinction coefficients by which the absorption data obtained from the FT-IR optical system are converted to quantitative compositional information.

The augmented form of the apparatus shown in FIG. 3 is operated in much the same way, with the exception that, at a certain point or at given intervals, the valve 74 associated with the gas supply 76 is operated to permit a charge of oxygen to be added to the mixture of carrier gas and volatiles produced in the lower section 68 of the furnace. The heating element 66 is cooperatively controlled so as to maintain suitable conditions (e.g., a temperature of 750° Centigrade) for oxidation of the components of the fluid mixture as the same flows upwardly into the optical cell 10. The oxygen supply may either be provided on a continuous basis, so that only oxidized products are received in the cavity 52, or it may be operated intermittently, so as to cause the gas stream to contain the unconverted volatiles during one interval and the oxidized products during the next. A two-minute cycle (one minute on, one minute off) can be used, and the power to the heater 66 will be varied on the same cycle so as to create an efficient oxidation environment without unduly influencing the pyrolysis reaction temperature conditions; shorter or longer cycles may of course be more desirable, depending upon the sample heating rate. In this way it is possible to combine two experiments in a single run, so as to not only identify the compounds evolved, but also to provide an elemental analysis of the volatiles, for carbon, hydrogen, nitrogen, sulphur and other IR-active gases.

The apparatus can be utilized to good advantage by introducing oxygen through the inlet pipe 30 at the completion of the pyrolysis reaction. Generally, this will be done by admixing approximately four percent by volume of oxygen into the helium carrier gas, and incrementally increasing the temperature (e.g., at a rate of 30 Centigrade degrees per minute) from about 250° to 900° or 1,000° Centigrade, so as to effect combustion of the char or other residue remaining in the sample holder after all volatiles have been driven off. By adding this step to the process, data as to the elemental make-up of the residue can be obtained, so as to enable a complete analysis of the sample to be made in a single run. Char reactivity and active site information can also be obtained by the same procedure, and similar data can be obtained from isothermal combustion reactions, typically carried out at temperatures in the range 300°–450° Centigrade.

In actual practice, the quartz tube of which the furnace shell is comprised may be about one foot in length and about one inch in diameter, with a spherical upper end to provide a ground-glass, ball-and-socket connection directly to the optical cell, which may be made of Pyrex and fitted with a collar for receipt of the spherical end of the furnace tube. The passage through the furnace tube may be of uniform diameter along its entire length; in any event, however, it is important that the cross-sectional area onto decrease from about the location at which the sample holder is to be suspended (and preferably, from a short distance below that level), through the inlet to the optical cell chamber. This is to avoid constricting the flow of fluids from the pyrolysis zone and to avoid the creation of turbulence, both of which effects could alter the physical state of the fluid constituents and could impede the complete introduction thereof into the optical cell, in turn diminishing the accuracy of the analysis and the value of the data obtained. Although a double-pass, center-focus optical system has been illustrated, it will of course be appreciated that multiple pass cells, with suitable transfer optics, and other appropriate arrangements may be substituted.

The heating element for the carrier gas and sample may be provided as an assembly of a pair of copper rods inserted into the tube passageway, with a Nichrome ribbon element, typically ⅜-inch wide and three to four feet long, wound about it in a double-helical configuration; the copper rods function as electrodes for attachment of the power supply to the heater. The element 66, for maintaining oxidation temperatures, may simply be a Nichrome ribbon coil (as may in fact be the element 46). Although preferably contained within the tube passageway, it may, if so desired, be wound about the outside since the primary function of the heater 66 is to maintain the tube at a high temperature. Other heater element geometries may of course be employed, and may (as in the case of a cylindrical form) be preferred in some instances.

Because the element 42, by which the sample holder 40 is suspended, is subjected to current flowing through the coils of the heater 66, it is desirably of a non-magnetic composition, such as Chromel wire; alternatives will however be readily apparent to those skilled in the art. The balance 14 may be of any suitable design, the commercially available Mettler Instruments Corporation Model AE160 balance being an example. For purposes of the present invention, however, such units must be modified to permit a flow-through of gas; the gas supply, which will normally be helium, serves not only to purge the balance but also to maintain the system in a pressurized, sealed condition.

Similarly, any suitable FT-IR spectrometer may be used, the IBM Instruments Model IT-85 being an example. Typically, the FT-IR will be capable of obtaining spectra every 0.2 second, to quantitatively determine the evolution rate and composition of the pyrolysis products. The computer, power supply, furnace and thermocouple system should allow the sample to be heated on a preprogrammed temperature profile at rates between three Centigrade degrees per minute and 100 Centigrade degrees per second, at temperatures between 20° Centigrade and at least 1,000° Centigrade, and to be held at those levels for selected periods of time.

A wide range of information can be obtained utilizing the instrument of the present invention. As indicated above, determinations can be made of moisture, volatiles, combustibles, char and ash of which a sample is composed (i.e., "proximate" analyses, in the case of coal), as can elemental analyses of volatile products evolved during pyrolysis of the sample material ("ultimate" analysis of coal samples) and elemental analyses of residues. The reactivity and active site density of char can also be determined by observations as to oxygen absorption and rate of combustion upon sample heating. Char combustion performance in commercial practice can be predicted based upon the information obtained. Calorific values can be calculated from elemental analyses, the total mineral composition of a sample can be determined based upon IR spectra, the concentration of IR-active minerals can be determined by use of standard potassium bromide pellet techniques, and sulphur forms can be identified. In addition, the method permits the elements analysis of tar and other condensible fractions, it enables functional group composition to be determined, and it permits flammability data to be derived. Finally, using the technique of the invention, investigations can be made into chemical kinetics and mechanisms, in regard to pyrolysis of the sample and the composition of the evolving gases.

EXAMPLE ONE

A bituminous coal is analyzed using an instrument in the form shown in FIGS. 1 and 3 of the drawings. To do so, a 200 milligram particulate sample of about 200-235 mesh size is placed into the sample holder 40, and is initially subjected to pyrolysis conditions. Thus, helium is introduced into the furnace 28 through the lower pipe 30 at a flow rate of about 1.2 liters per minute, and power is supplied to the lower heater 46 so as to gradually elevate the temperature of the sample and the carrier gas from ambient to 900° Centigrade at a constant rate of 30 Centigrade degrees per minute, the only deviation being that the temperature is held constant at about 150° Centigrade for about three to four minutes to drive off moisture.

After reaching 900°, the pyrolysis reaction is deemed complete. Then, the temperature is reduced to about 250° Centigrade, and about four volume percent of oxygen is added to the helium flow through the pipe 30; the temperature of the sample is again increased, at the same constant heating rate, to 900° Centigrade, thereby causing combustion of the char remaining in the sample holder.

Utilizing a fresh sample of the same material, the pyrolysis reaction is repeated. In this phase of the example, however, pure oxygen is introduced through the pipe 32 at such a rate as to produce a concentration of about 10 percent by volume, based upon the total amount of helium and oxygen introduced. Also, the upper heater 66 is maintained at 750° Centigrade to ensure oxidation of the volatiles evolved from the sample.

From the weight loss data provided by the balance, and the spectrometric data as to species and amounts of gases evolved n the straight pyrolysis reaction, the proximate analysis of the sample is determined to be (on a weight basis): 0.51% moisture, 10.92% ash, 25.23% total volatiles, and 63,34% fixed carbon. The volatile fraction is more specifically found to be composed (based upon the dry, ash-free sample weight) of: 0.92% carbon monoxide, 1.28% carbon dioxide, 1.84% methane, 0.99% water, 0.20% ethylene, 1.04% sulfur dioxide, 0.14% cyanide, 0.06% carbonyl sulfide, 1.98% hydrogen, and 19.45% tar. Analysis of the gases produced in the volatiles oxidation reactions show the following elemental composition (dry, ash-free sample weight basis): 19.41% carbon, 4.76% hydrogen, 2.30% oxygen, 0.91% nitrogen, and 1.10% sulfur. The char oxidation gases indicate the following elemental constituents, again expressed as weight percentages of the dry, ash-free sample: 67.37% carbon, 0.54% hydrogen, 1.03% oxygen, 0.77% nitrogen, and 1.80% sulfur. These elemental analysis data are found to be in close agreement with data obtained by standard analytical techniques.

Similarly analyses of oil shales and petroleum source rocks provide valuable data as to organic structure, yield and reactivity.

One of the primary advantages of coupling the TGA functions is in compensating for an inherent limitation of FT-IR spectrometry, i.e., its inability to identify, or insensitivity to, certain species, such as free hydrogen and hydrogen sulfide. By indicating that a substance that was not reflected in the spectrometric data had in fact been evolved, the TGA data, taken in conjunction with the oxidation cycle by which hydrogen would be converted to water, and hydrogen sulfide would be converted to water and sulfur dioxide, provide the information necessary to enable a thorough analysis of the sample to be made.

A unique feature of the invention is that it affords an integrated system, which utilizes the computer of the FT-IR apparatus to provide all control and analyses functions. Thus, it can be programmed to control the temperature excusion of the sample and the carrier gas, the conditions for oxidation of the evolved products and the solid residue, and the flow of gases introduced into the furnace. At the same time, signals from the temperature sensor and balance, as well as the FT-IR data, can be plotted or printed-out to present the analytical information sought in a most useful form.

Another unique feature of the instrument is its self-calibration capability. This may be done by subjecting a solid calibrating compound, of known composition, to pyrolysis conditions, following a suitable temperature profile. Through a least squares optimizing routine, programmed into the FT-IR computer, the measured weight loss data from the balance can be employed to adjust the extinction coefficients that are applicable to the FT-IR wavenumber-dependent absorption curves from which the quantitative analysis data are derived. The same approach can be employed utilizing, as the pyrolysis sample, a material that is of substantially known composition, but that contains trace amounts of unknown constituents.

The use of helium as the inner carrier gas is particularly desirable, not only because it permits all of the reaction products to be swept into the optical cell of the FT-IR unit, but also because it causes the condensible fractions of the volatiles to convert to a highly desirable aerosol form, comprised of droplets that are two microns or less in size. This is believed to be attributable to the high thermal conductivity and low heat capacity of helium, which cause rapid cooling and condensation in the form of a fine mist. In any event, it allows the optical system to analyze the condensible volatiles most effectively, because they will flow with the gas stream rather than precipitating upon the walls of the system, and because light scattering is minimized. Maintaining the optical cell at a temperature of 100°-150° Centigrade ensures that any water in the fluid stream will remain in vaporous form.

Thus, it can be seen that the present invention provides a novel apparatus and method by which solid and liquid materials can be analyzed at high rate of speed, to provide information concerning composition, structure, reaction mechanisms and kinetics, and the like. The method and apparatus combine principles of thermogravimetric and Fourier-transform infrared analyses in a highly effective and desirable manner, and are particularly well-suited for the analyses of typical insoluble hydrocarbons. The products evolved by pyrolysis of the sample are introduced into the optical cell completely and in an optimal form for analysis. Proximate and ultimate analyses can be performed on coal, and comparable analyses can be carried out on other substances, using the present method and apparatus, and determinations of calorific value, char reactivity, active site density, sulphur form identification, and other characterizing features of such materials can be made as well.

Having thus described the invention, what is claimed is:

1. Analytical apparatus comprised of:
   (a) a furnace having an internal chamber with an inlet, and an outlet spaced from said inlet, defining a path for fluid flow therebetween through said chamber;
   (b) an optical analysis cell having an enclosed cavity with an inlet and an outlet for fluid flow therethrough, said cell cavity being in substantially direct flow communication with said furnace chamber through said inlet of said cell cavity and said outlet of said furnace chamber;
   (c) an infrared spectrometer operatively connected to said optical cell for obtaining compositional data from substances passing through said cavity thereof;
   (d) heating means including a heater having heating elements defining a portion of said path within said furnace chamber and adapted to heat gas flowing therealong, and including temperature control means for controlling the temperature of said heating means; and
   (e) weighing means, including a balance and a sample holder operatively connected thereto, said sample holder being adapted to afford efficient heating of material held thereby, and being disposed within said furnace chamber at a location along said path portion defined by said heater elements and spaced from said chamber inlet a distance sufficient to preheat fluid flowing along said path portion to substantially the temperature of said heater elements prior to contact with said sample holder, said apparatus being substantially free from constriction along said furnace path, from the vicinity of said holder location and through said chamber outlet and said cell cavity inlet.

2. The apparatus of claim 1 additionally including temperature sensing means disposed adjacent said sample holder.

3. The apparatus of claim 1 wherein said weighing means includes means for generating an electrical signal indicative of the weight change of a sample contained within said holder, as a function of time.

4. The apparatus of claim 1 wherein said furnace has a second inlet to said chamber disposed along said path between said first-mentioned inlet and said outlet and spaced, with respect to said first-mentioned inlet, beyond said sample holder.

5. The apparatus of claim 4 wherein said heating means includes a second heater having elements disposed between said first-mentioned heater elements and said outlet of said furnace chamber and defining a second path portion therewithin adjacent said first path portion and aligned therewith, said second heater elements being adapted to heat fluid flowing along said second path portion, said temperature control means being adapted to independently control the temperatures of said first and second heaters, said second gas inlet being disposed substantially at the intersection of said two path portions.

6. The apparatus of claim 1 wherein said infrared spectrometer is a Fourier-transform spectrometer.

7. The apparatus of claim 6 wherein said spectrometer incorporates computer means for comparing, by a least squares optimizing routine, weight change data from said weighing means with quantitative compositional data from substances passing through said cell cavity, and for adjusting extinction coefficients applicable to the absorption curves from which such data are determined by said spectrometer, and thereby to enable self-calibration of said apparatus, said weighing means being adapted to generate a signal indicative of the weight change of sample contained within said holder, as a function of time, and to provide the same to said computer means.

8. The apparatus of claim 1 wherein said chamber is of elongated and generally rectilinear form.

9. The apparatus of claim 8 wherein said optical analysis cell has second heating means associated therewith, and is adapted to pass electromagnetic radiation through said cavity thereof along axes that are substantially perpendicular to the longitudinal axis of said furnace chamber.

10. The apparatus of claim 8 wherein said chamber is vertically oriented, with said inlet to said chamber being disposed adjacent the lower end and said outlet therefrom being at the upper end thereof, said sample holder being suspended within said furnace chamber.

11. The apparatus of claim 10 wherein said cell is connected directly to the top of said furnace, with said chamber outlet and cavity inlet being of substantially the same cross-sectional area, said cell being elongated in a direction substantially perpendicular to said axis of said furnace cavity and having said inlet and outlet adjacent opposite ends and disposed at the bottom and top, respectively, of said cavity.

12. Analytical apparatus comprised of:
(a) a furnace having an internal chamber with an inlet, and an outlet spaced from said inlet, defining a path for fluid flow therebetween through said chamber;
(b) an optical analysis cell having an enclosed cavity with an inlet and an outlet for fluid flow therethrough, said cell cavity being in substantially direct flow communication with said furnace chamber through said inlet of said cell cavity and said outlet of said furnace chamber;
(c) a Fourier-transform infrared spectrometer operatively connected to said optical analysis cell for obtaining compositional data from substances passing through said cavity thereof;
(d) heating means, including a heater having heating elements defining a portion of said path within said furnace chamber and adapted to heat gas flowing therealong, and including temperature control means; and
(e) weighing means, including a balance and a sample holder operatively connected thereto, said sample holder being adapted to afford efficient heating of material held thereby, and being disposed within said furnace chamber at a location along said path portion defined by said heater elements and so spaced from said chamber inlet as to enable preheating, by said heating elements, of fluid flowing along said path portion prior to contact with said sample holder, said apparatus being substantially free from constriction along said furnace path, from the vicinity of said holder location and through said chamber outlet and said cell cavity inlet.

13. An analytical method comprising the steps of:
(a) supporting a sample of a material to be analyzed within the chamber of a furnace, said sample being subject to pyrolysis to evolve volatiles;
(b) heating said sample within said furnace chamber to effect pyrolysis thereof and thereby to evolve volatiles;
(c) sweeping said pyrolyzing sample with a carrier gas;
(d) monitoring the weight change of said pyrolyzing sample as a function of time;
(e) introducing the resultant mixture of said carrier gas and said evolved volatiles directly into the cavity of an optical analysis cell, and determining by infrared spectrometry the composition of said volatiles as a function of time; the flow rate, temperature thermal conductivity and heat capacity of said carrier gas being such as to cause any components of said mixture that are condensible at the temperature prevailing in said optical cell to condense to form an aerosol; and
(f) correlating the dynamic weight change data and the dynamic compositional data for analysis of said sample.

14. The method of claim 13 wherein said temperature of said gas and of said sample are increased at a constant rate.

15. The method of claim 13 wherein said gas and sample are heated by subjecting them to a common thermal energy radiator within said furnace chamber, said sample being disposed adjacent said radiator and said gas being passed therealong prior to contacting said sample so as to preheat said gas and ensure that said gas and sample will be at substantially the same temperature at the point of initial contact.

16. The method of claim 13 wherein said carrier gas is helium and wherein said analysis cell is heated to a temperature of about 100° to 150° Centigrade, said gaseous mixture entering said analytical cell cavity in laminar flow.

17. The method of claim 13 wherein in said step (e), said volatiles composition determination is made by Fourier-transform infrared spectrometry.

18. The method of claim 13 wherein said sample is of substantially known composition, and wherein the weight change data from said monitoring step (d) are compared with quantitative data obtained in said step (e) determination, and are utilized to adjust the extinction coefficients applicable to the wavenumber-dependent absorption curves from which said quantitative date are determined.

19. The method of claim 13 wherein a residue is produced in said step (b), and including the additional step, carried out subsequent to the substantially complete pyrolysis of said sample, of introducing oxygen into said residue under conditions appropriate to effect oxidation thereof.

20. The method of claim 19 wherein said additional step is carried to under controlled temperature conditions, so as to enable an evaluation to be made of the reactivity of said residue.

21. The method of claim 20 wherein said controlled temperature conditions comprise a progressive increase in the temperature of said residue, at a predetermined rate, from about 250° to at least about 900° Centigrade.

22. An analytical method comprising the steps of:
(a) supporting a sample of a material to be analyzed within the chamber of a furnace, said sample being subject to pyrolysis to evolve volatiles;
(b) heating said sample within said furnace chamber to effect pyrolysis thereof and thereby to evolve volatiles;

(c) sweeping said pyrolyzing sample with a carrier gas preheated to the temperature of said pyrolyzing sample;
(d) monitoring the weight change of said pyrolyzing sample as a function of time;
(e) introducing the resultant mixture of said carrier gas and said evolved volatiles directly into the cavity of an optical analysis cell, and determining the composition of said volatiles, as a function of time, by Fourier-transform infrared spectrometry; the flow rate, thermal conductivity, temperature, and heat capacity of said gas being such as to cause any components of said mixture that are condensible at the temperature prevailing in said optical cell to condense to form an aerosol; and
(f) correlating the dynamic weight change data and the dynamic compositional data for analysis of said sample.

23. An analytical method comprising the steps of:
(a) supporting a sample of a material to be analyzed within the chamber of a furnace, in a quantity suitable for thermogravimetric analysis, said sample being subject to pyrolysis to evolve volatiles;
(b) heating said sample within said furnace chamber to effect pyrolysis thereof and thereby to evolve volatiles;
(c) sweeping same sample with helium gas flowing at 0.5 to 2 liters per minute and preheated to the temperature of said sample;
(d) monitoring, by thermogravimetric means, the weight change of said pyrolyzing sample as a function of time;
(e) introducing the resultant mixture of said carrier gas and said evolved volatiles directly into the cavity of an optical analysis cell, and determining by infrared spectrometry the composition of said volatiles as a function of time, substantially all components of said mixture that are condensible at the temperature prevailing in said optical cell condensing to particles of less than about five microns in size upon entry thereinto; and
(f) correlating the dynamic weight change data to the dynamic compositioal data for analysis of said sample.

24. The method of claim 23 wherein said analysis cell is heated to a temperature of about 100° to 150° Centigrade, wherein said sample quantity is 200 milligrams, and wherein said volatiles composition determination is made by Fourier-transform infrared spectrometry.

25. An analytical method comprising the steps of:
(a) supporting a sample of a material to be analyzed within the chamber of a furnace, said sample being subject to pyrolysis to evolve volatiles;
(b) heating said sample within said furnace chamber to effect pyrolysis thereof and thereby to evolve volatiles;
(c) sweeping said pyrolyzing sample with a carrier gas preheated to the temperature of said pyrolyzing sample to produce a resultant mixture thereof;
(d) monitoring the weight change of said pyrolyzing sample as a function of time;
(e) introducing a quantity of oxygen into said resultant mixture during part of the time that said sample is pyrolyzing, said quantity of oxygen and the temperature at which the resultant fluid is maintained during said part of the time being sufficient to effect substantially complete oxidation of said volatiles, and to produce a final gaseous mixture, said oxygen-containing mixture being supplementally heated so as to maintain said sufficient temperature, and said oxygen introduction and said supplemental heating being simultaneously and intermittently commenced and terminated;
(f) introducing said final gaseous mixture into the cavity of an optical analysis cell, and determining the composition of said volatiles, in both the oxidized and the unoxidized state, on an intermittent basis and as a function of time; and
(g) correlating the dynamic weight change data and the dynamic compositional data for analysis of said sample.

* * * * *